(12) United States Patent
Laguna (10) Patent No.: US 11,191,929 B2
(45) Date of Patent: *Dec. 7, 2021

(54) APPARATUS AND METHODS FOR ENHANCED DRUG DELIVERY

(71) Applicant: Sentient Holdings, LLC, Flagstaff, AZ (US)

(72) Inventor: Alvaro J. Laguna, Flagstaff, AZ (US)

(73) Assignee: Sentient Holdings, LLC, Flagstaff, AZ (US)

( * ) Notice: Subject to any disclaimer, the term of this patent is extended or adjusted under 35 U.S.C. 154(b) by 329 days.

This patent is subject to a terminal disclaimer.

(21) Appl. No.: 16/361,706

(22) Filed: Mar. 22, 2019

(65) Prior Publication Data

US 2019/0282790 A1   Sep. 19, 2019

Related U.S. Application Data

(63) Continuation of application No. 15/351,561, filed on Nov. 15, 2016, now Pat. No. 10,293,144.

(60) Provisional application No. 62/256,396, filed on Nov. 17, 2015.

(51) Int. Cl.
*A61M 25/10* (2013.01)
*A61M 25/00* (2006.01)

(52) U.S. Cl.
CPC ..... *A61M 25/10* (2013.01); *A61M 2025/0057* (2013.01); *A61M 2025/105* (2013.01); *A61M 2025/1075* (2013.01); *A61M 2025/1081* (2013.01); *A61M 2025/1086* (2013.01)

(58) Field of Classification Search
CPC .... A61M 2025/1081; A61M 2025/105; A61M 2025/1075; A61M 2025/1086; A61M 25/10
See application file for complete search history.

(56) References Cited

U.S. PATENT DOCUMENTS

| 5,213,576 | A | 5/1993 | Abiuso et al. |
| 10,293,144 | B2 * | 5/2019 | Laguna ................ A61M 25/10 |
| 2005/0177226 | A1 | 8/2005 | Banik et al. |

(Continued)

FOREIGN PATENT DOCUMENTS

CN    203724603 U    7/2014

OTHER PUBLICATIONS

EPO, extended European search report issued on EP patent application No. 16867032.1, dated Jun. 5, 2019, 9 pages.

(Continued)

*Primary Examiner* — Nathan R Price
*Assistant Examiner* — Anh Bui
(74) *Attorney, Agent, or Firm* — Greenberg Traurig, LLP (57) ABSTRACT

Systems and method for using a sleeve for enhanced drug delivery are described. The sleeve may incorporate porous materials and may be coated or treated with various drugs and/or therapeutic agents. The sleeve may be utilized in cooperation with balloon catheters and/or other devices. When acting as a reservoir for holding various drugs and/or therapeutic agents, the drug delivery sleeve provides a means of reducing drug losses as well as a controlled mechanism for drug release. The materials for the sleeve, constructed by various techniques, may be circumferentially distensible, may be elastic, and may have varying degrees of recoil as needed for any particular purpose.

29 Claims, 7 Drawing Sheets

(56) References Cited

U.S. PATENT DOCUMENTS

2005/0273075 A1 12/2005 Krulevitch et al.
2013/0253426 A1 9/2013 Campbell et al.

OTHER PUBLICATIONS

ISA/US, international Search Report and Written Opinion issued on PCT application No. US16/62252, dated Feb. 15, 2017, 16 pages.
CNIPA, office action issued on Chinese patent application No. 201680062809.4, dated Jul. 1, 2020, 12 pages.

* cited by examiner

APPARATUS AND METHODS FOR ENHANCED DRUG DELIVERY

RELATED APPLICATION INFORMATION

This application claims the benefit of and is a continuation of U.S. application Ser. No. 15/351,561, filed on Nov. 15, 2016, which application claims the benefit of U.S. Provisional Application No. 62/256,396, filed on Nov. 17, 2015, the disclosures of which are incorporated herein by reference in their entirety.

BACKGROUND

The following disclosure generally relates to medical devices.

Vascular disease, the disease of blood vessels, is one of the leading causes of death in the western world. There are two main categories of vascular disease, aneurysmal and occlusive. Aneurysmal disease results in the weakening of blood vessels causing them to dilate excessively and in some instances ultimately rupture. Occlusive disease results in blockage of blood vessels, limiting the conveyance of blood.

Balloon dilation is a commonly used treatment for blood vessels ravaged by occlusive disease and for other tubular structures within the body suffering from a variety of maladies. Balloon catheters have been employed successfully to radially open various bodily conduits. In the treatment of occlusive vascular disease, balloon dilation of blood vessels (angioplasty), remodels the inner surface of the blocked vessels, restoring blood flow. Additionally, balloon dilation is practiced in other bodily conduits such as the urinary tract, the bile duct, tear ducts, nasal and sinus passages and the tracheo-bronchial tree.

Currently, it is common procedure to combine site specific drug therapy with balloon dilation. To such ends, balloon catheters are equipped with various means for the conveyance of therapeutic agents to a site of disease. Some devices include channels through which a liquid drug can be delivered. In some cases, unique compositions of drugs are applied onto the balloon surface and are conveyed to the site of disease by direct contact during the balloon dilation.

Regardless of the method of delivery, controlling the amount of drug delivered to the site is challenging. If the drug is conveyed through a channel, it is difficult to ensure that contact between the drug and the disease is of adequate duration and intimacy to be effective. If the drug is applied onto the surface of the balloon, the drug gets washed away (at least partially) by various bodily fluids and/or fluids introduced procedurally during the navigation of the balloon to the site. Also, if the drug is applied onto the surface of the balloon, the drug coating may get scraped off by other devices or by bodily structures other than the site of disease. In any case, it is difficult to predict exactly how much drug is being delivered to the intended site and whether the dosage is sufficient. In the face of such uncertainty, the strategy typically employed is to use an overabundance of drug to accommodate the described losses in the hope that a successful therapeutic outcome results.

It is desirable to create a device that alleviates the challenges outlined above.

SUMMARY

A sleeve according to various described embodiments acts as a protective layer and/or as a vehicle for the delivery of drugs and/or therapeutic agents. The sleeve may be constructed of porous materials and may be rendered porous by suitable means. Materials that may be used to produce the sleeve may be distensible and may provide characteristics such as enhanced flexibility, kink resistance, and/or limited foreshortening as needed for any particular purpose. By way of example only, the sleeve may be produced from materials treated to circumferentially distend without significant foreshortening and may exhibit varying degrees of recoil. The sleeve may also be produced from elastic materials.

The sleeve may be fitted over the balloon section of any suitable balloon catheter. The sleeve acts as a barrier between the balloon and any fluids and/or bodily structures other than the targeted disease site as well as adjunct devices that may be encountered during the course of the balloon dilation procedure. In this manner, the sleeve is a means of reducing drug losses.

In various embodiments, drugs and/or any suitable therapeutic agents may be resident on any surface of the sleeve including within the porous sleeve structure and/or on any surface of the balloon catheter. In certain embodiments, the sleeve may act as a drug reservoir, enabling greater amounts of drug to be delivered to the disease site. Additionally, in embodiments where the drug is within the porous structure of the sleeve, the drug is safe from being washed and/or scraped away as previously mentioned. In certain embodiments, the distention of the sleeve, caused by the inflation of the underlying balloon results in a general increase in the sleeve porosity which when coupled with the pressure exerted by the underlying balloon, causes the drug, resident on any suitable surface, to be released.

Thus the described sleeve may act as a means of reducing drug losses as well as acting as a reservoir for holding the drug. Furthermore, the described sleeve, working cooperatively with a balloon catheter, provides a controlled mechanism for the release of the drug. The described sleeve may also be combined and act cooperatively with any other suitable device resulting in enhanced drug delivery.

BRIEF DESCRIPTION OF THE EXEMPLARY DRAWINGS

Additional aspects of the disclosed embodiments will become evident upon reviewing the non-limiting descriptions set forth in the specification and claims, in conjunction with the accompanying figures, wherein like numerals designate like elements and wherein:

It is to be noted that elements in the figures are illustrated for simplicity and clarity and have not necessarily been drawn to scale. For example, the dimensions of some of the elements in the figures may be exaggerated relative to other elements to help improve understanding of embodiments described herein.

DETAILED DESCRIPTION

Various aspects and features disclosed hereinafter may be described in terms of functional components and steps. Such functional components and steps may be realized by any number of elements and/or steps configured to perform the specified functions. For example, the present drug delivery sleeve may employ balloon catheters, which may carry out a variety of functions in various embodiments, applications, and environments. Also, the drug delivery sleeve may be coated/treated with any suitable drug and/or therapeutic agent intended to alleviate any applicable disease. Furthermore, the drug delivery sleeve may be treated by any suitable means such that it interacts with fluids in a manner that optimizes the delivery of the drug and/or therapeutic agent. In addition, the described drug delivery sleeve may be practiced in conjunction with any number of procedures, systems and adjunct devices. The embodiments described are merely exemplary applications. Further, the described drug delivery sleeve may employ any number of techniques, conventional or otherwise, for placement, use, manufacturing, and the like. Such general techniques that may be referred to may not be described in detail.

A drug delivery sleeve according to various aspects of the disclosed embodiments is intended for use within an organism, such as a human being or animal. The drug delivery sleeve may be used in any part of the organism, for example in blood vessels, bile ducts, the urinary tracts, nasal passages, sinuses or any other conduit or structure in the organism. The drug delivery sleeve may be configured in any manner according to the particular application or environment, including variations in dimensions, shape, materials, flexibility, and the like. Various aspects of the disclosed embodiments may also be applicable to other devices, such as other medical devices and other conduits.

Figure 1:
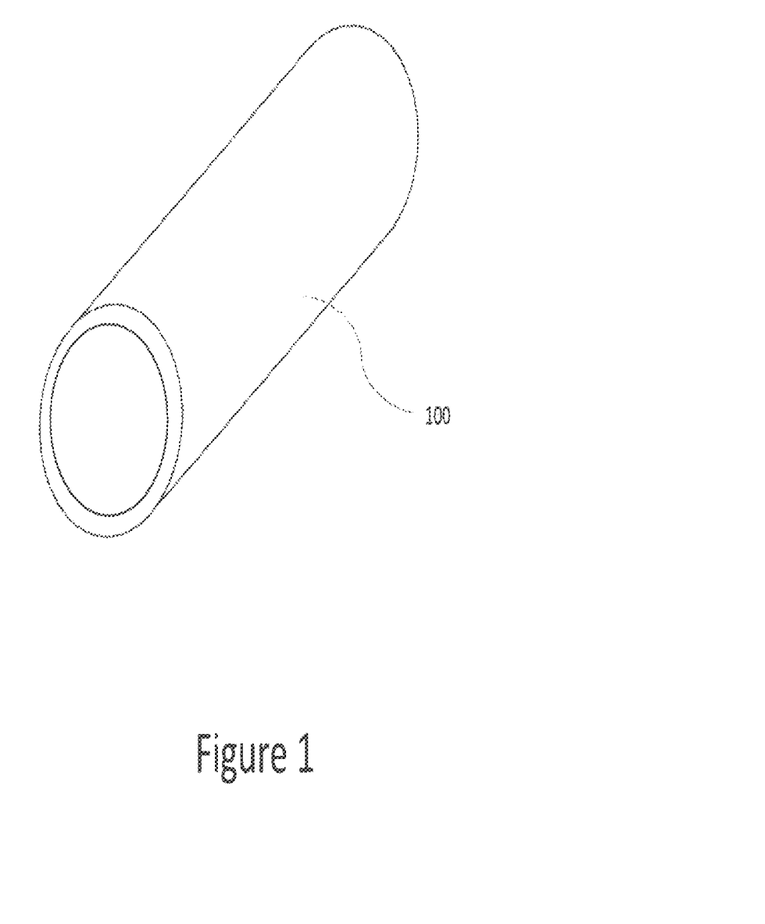
FIG. 1 is a perspective view of an exemplary embodiment of a drug delivery sleeve.
Figure 2:
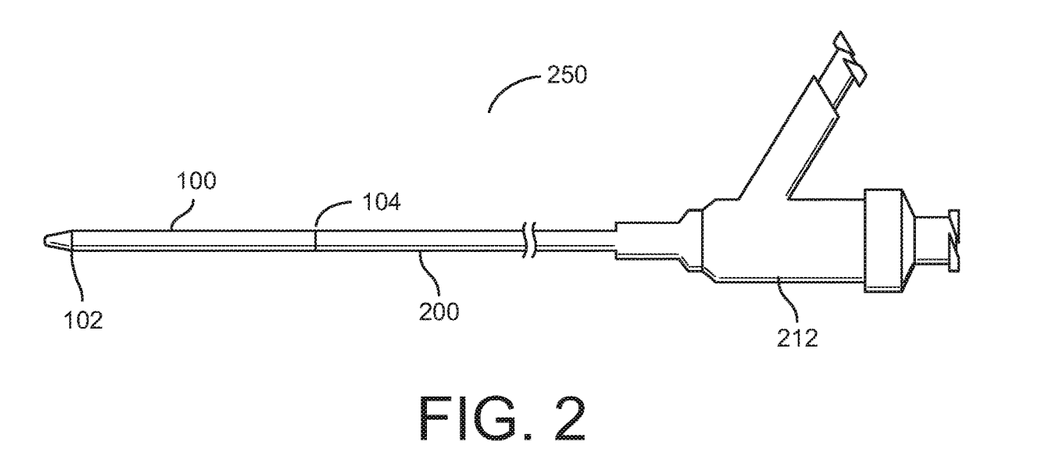
FIG. 2 is a side view of an exemplary embodiment of a drug delivery sleeve mounted on a balloon catheter.

Referring to FIG. 1 and FIG. 2, a drug delivery sleeve 100 may be generally tubular in shape with two open ends and generally fitted onto a balloon catheter 200. Drug delivery sleeve 100 may be created from any suitable material or combination of materials. For instance, drug delivery sleeve 100 may be created from materials such as but not limited to nylon, polyethylene, PolyEthylene Terephthalate (PET), carbon, kevlar, PolyEther Block Amid (PEBA), silicone, polyurethane, latex, flouroelastomers of all types, PolyEtherEtherKetone (PEEK) and/or PolyTetraFluoroEthylene (PTFE) as well as other flouropolymers. Certain embodiments of drug delivery sleeve 100 may include porous elastomeric materials such as but not limited to porous silicone and porous polyurethane. In certain embodiments it may also be advantageous to include various metals within drug delivery sleeve 100.

Additionally, drug delivery sleeve 100 may be created from any suitable form or combination of forms of material. For example, drug delivery sleeve 100 may be created from forms such as but not limited to extruded tubing, tubing manufactured by dipping, spraying or molding, textile materials of all sorts, non-woven materials, electro spun materials, sponge-like materials, various foams, membranes, films and the like. Preferably, drug delivery sleeve 100 is produced from inherently porous materials and/or materials rendered porous by various means. For example extruded tubing may be laser cut to create a suitably porous form.

Figure 8:
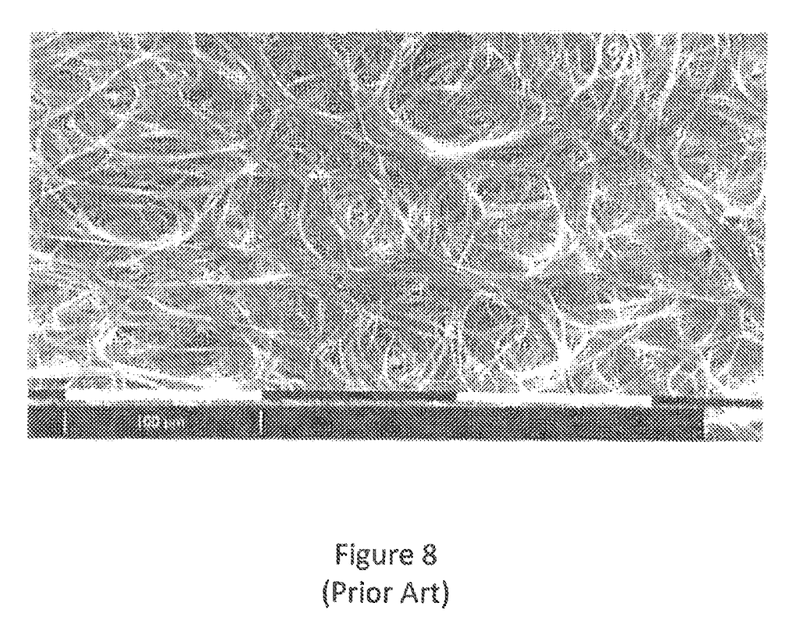
FIG. 8 illustrates a magnified view of a piece of prior art Solupor material showing the porous microstructure of the material prior to processing according to the description contained herein.

A first preferred embodiment of drug delivery sleeve 100 is made from porous circumferentially distensible polyethylene tubing as described in U.S. Pat. No. 6,949,121 to Laguna, incorporated herein by reference. Referring to U.S. Pat. No. 6,949,121, the exemplary embodiment of drug delivery sleeve 100 is produced by generally following the process outlined in steps 1416 through 1438 of FIGS. 14A and 14B with the following notable exceptions. The exceptions are that Solupor 3P07A porous polyethylene film is used and that the rectangular piece used to form the distensible tube (or "side-branch tube" as it is called in U.S. Pat. No. 6,949,121) has 230×156 mm dimensions and is wrapped around a mandrel having an outer diameter of about 6.9 mm, resulting in a film thickness of approximately six layers. Additionally, referring to step 1418 of U.S. Pat. No. 6,949,121, the approximately six layers of film are bonded together in an air convection oven set at 140° C. for 10 minutes. Finally, referring to step 1428 of U.S. Pat. No. 6,949,121, an additional stage of circumferential distention is added: after the tube is distended over the 4 mm outer diameter tapered mandrel (step 1428), it is distended again, this time over a 6 mm outer diameter tapered mandrel. The resulting distensible tube has an approximate inner diameter of 1.2 mm, an approximate wall thickness of 0.05 mm and is capable of being distended to a 5 mm inner diameter reliably. A magnified view of a piece of Solupor porous polyethylene material showing the porous microstructure of the material prior to the above described processing is shown in FIG. 8.

To complete the preferred embodiment of drug delivery sleeve 100, the distensible polyethylene tube is coaxially fitted over a 1.0 mm diameter stainless steel rod and compressed radially to fit snugly on the rod using a handheld stent crimper manufactured by Machine Solutions Inc., located in Flagstaff, Ariz. With the radial compression complete, the finished first preferred embodiment of drug delivery sleeve 100 is circumferentially distensible with minimal foreshortening and recoil, has an approximate inner diameter of 1.0 mm, an approximate wall thickness of 0.05 mm, and, having been produced from porous polyethylene film, has a porous structure.

There are various ways of applying a drug onto/into the surfaces of the preferred embodiment of drug delivery sleeve 100 and/or surfaces of balloon catheter 200. In a first embodiment, referring now to FIG. 3, the balloon component 202 of balloon catheter 200 is folded into a compact configuration and is already coated with any suitable drug by any suitable means. Balloon catheter 200, in this exemplary embodiment, may be of construction and materials typically encountered in balloon catheters designed for the purpose of angioplasty in peripheral vessels. For example, balloon catheter 200 may incorporate balloon 202, manufactured by blow molding, with a nominal inflated diameter of 4 mm, a nominal length of 40 mm, and a rated burst pressure of about 10 MPa (10 atm) or higher. One manufacturer of such peripheral balloon angioplasty catheters, with and without drug coatings, is Bard Peripheral Vascular, located in Tempe, Ariz.

Figure 3:
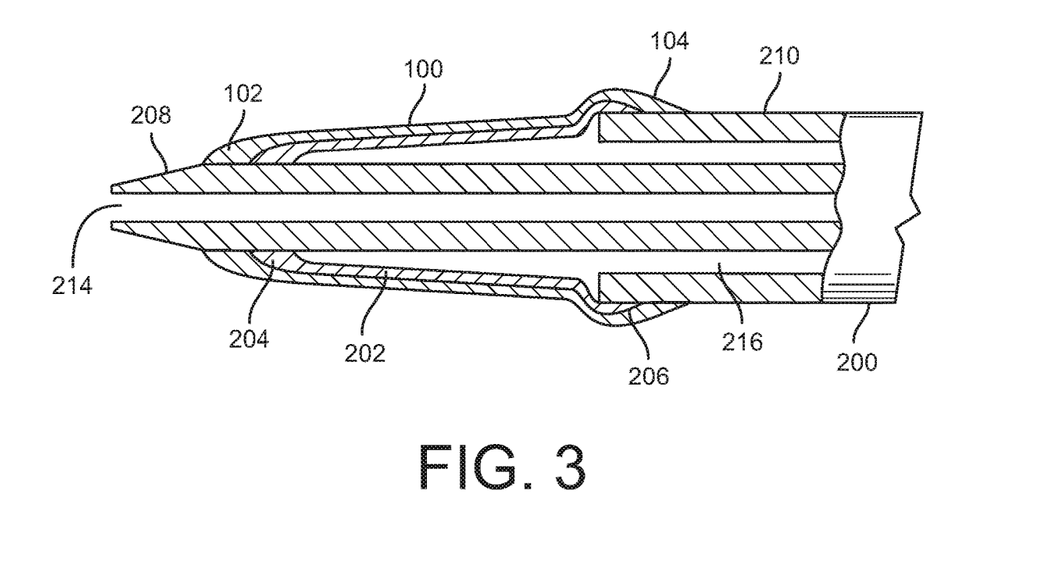
FIG. 3 is a cross-sectional view of an exemplary embodiment of a drug delivery sleeve attached to a balloon catheter.

There are various ways of attaching the preferred embodiment of drug delivery sleeve 100 to balloon catheter 200. In order to attach the preferred exemplary embodiment of drug delivery sleeve 100 to balloon catheter 200, a length of drug delivery sleeve 100 is cut such that the sleeve is longer than the length of balloon 202 plus the lengths of distal and proximal balloon seals 204 and 206 respectively. The length of drug delivery sleeve 100 is fitted coaxially over balloon 202 and balloon seals 204 and 206. Once properly situated, drug delivery sleeve 100 is attached to inner catheter member 208 to form distal sleeve attachment 102 and attached to outer catheter member 210 to form proximal sleeve attachment 104. With drug delivery sleeve 100 attached to balloon catheter 200 and balloon 202 already coated with a drug, a first exemplary embodiment of a drug delivery balloon catheter 250 is completed.

Although the embodiment of balloon catheter 200 depicted by FIG. 3 comprises two catheter members arranged coaxially, any suitable catheter member arrangement may be employed. For example, a single, dual-lumen catheter member, having a lumen providing communication between the balloon port and the balloon, and another lumen capable of accommodating a guidewire may be employed. Additionally, the assembly of the catheter member(s) may be of any suitable configuration such as, but not limited to, fixed wire, wherein a wire element is included into the catheter tube(s) to add stiffness, over the wire (as depicted by FIG. 2), or rapid exchange.

The design and manufacture of catheter components and assemblies thereof is well known. Catheter members 208 and 210 as well as balloon 202 may be of any suitable material or combination of materials such as, but not limited to, silicone, polyurethane, latex, nylon, polyethylene, PET, PEBA and other copolymers, PTFE and/or various other fluoropolymers, as well as metals. Additionally, catheter members 208 and 210 as well as balloon 202 may be created from any suitable form or combination of forms of material. For example, catheter members 208 and 210 as well as balloon 202 may be created from forms such as but not limited to extruded tubing, tubing manufactured by dipping, spraying or molding, textile materials of all sorts, non-woven materials, membranes, films and the like. In some embodiments, catheter members 208 and 210 may suitably contain metallic elements such as, but not limited to, braids, hypodermic tubing and/or wires as well as radiopaque markers of varying design. Proximal adapter 212 may be configured in any suitable manner and may also be of any suitable material or combination of materials such as, but not limited to, nylon, polycarbonate, polypropylene, PEBA, or polysulfone.

Any suitable method or combination of methods may be employed to create the attachments between the various elements of the balloon catheter 200. Such methods may include, but are not limited to, the use of various adhesives or thermal bonding techniques. Similarly, any suitable method or combination of methods may be employed to create distal and proximal sleeve attachments 102 and 104 respectively. Such methods may include, but are not limited to, the use of various adhesives, thermal bonding techniques, ligatures and/or swaged bands. As previously mentioned, in this exemplary embodiment, catheter members 208 and 210 are produced of materials typically found in peripheral balloon angioplasty catheters, materials that are typically melt processable. Since drug delivery sleeve 100, in this exemplary embodiment, is also made of a melt processable material, utilization of thermal bonding techniques to create sleeve bonds 102 and 104 may be preferred.

While creating sleeve attachments 102 and 104, particularly if thermal bonding techniques are utilized, care should be taken to avoid excessive deformation of catheter members 208 and 210 and to avoid collapse of lumens 214 and 216. For example, when creating distal sleeve attachment 102, a wire may be placed inside guidewire lumen 214 to ensure that the lumen is properly supported and does not collapse. In an over the wire catheter configuration, as shown by FIG. 2 for example, it may be advantageous to attach drug delivery sleeve 100 to catheter members 208 and 210 prior to the attachment of proximal adapter 212. If proximal adapter 212 is not attached, then, for example, a length of very thin walled metal hypodermic tubing may be fitted coaxially between inner catheter member 208 and outer catheter member 210 such that the hypodermic tubing supports inflation lumen 216 during the attachment of drug delivery sleeve 100 to outer catheter member 210. In embodiments where balloon catheter 200 has a rapid exchange configuration, it may be advantageous to complete the attachment of drug delivery sleeve 100 to a distal subassembly of balloon catheter 200. In such a case, the same techniques for supporting guidewire and inflation lumens 214 and 216 respectively may be employed. In certain instances, it may be preferable to use thin walled polymeric tubing such as polyimide tubing supplied by MicroLumen (located in Oldsmar, Fla.) in lieu of metal hypodermic tubing.

Figure 4:
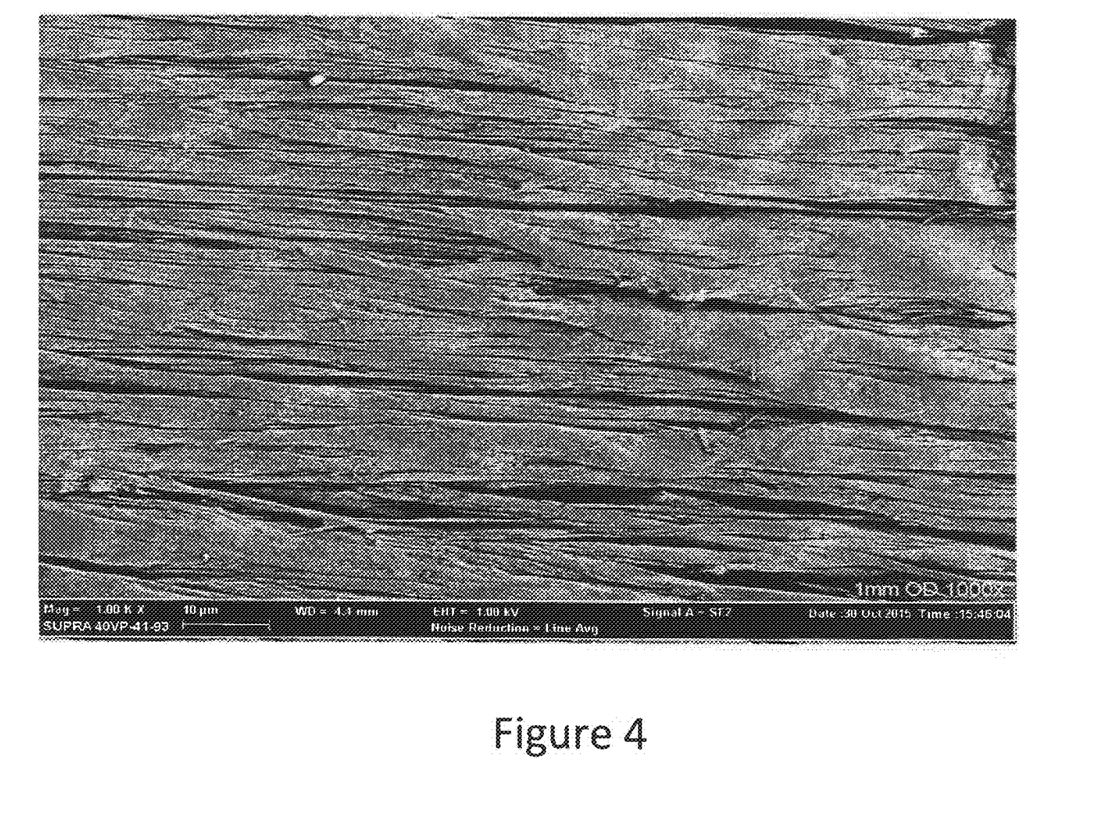
FIG. 4 is a scanning electron micrograph (SEM), at 1000× magnification, showing the porous structure of an exemplary embodiment of a drug delivery sleeve in its native state, prior to distention.
Figure 5:
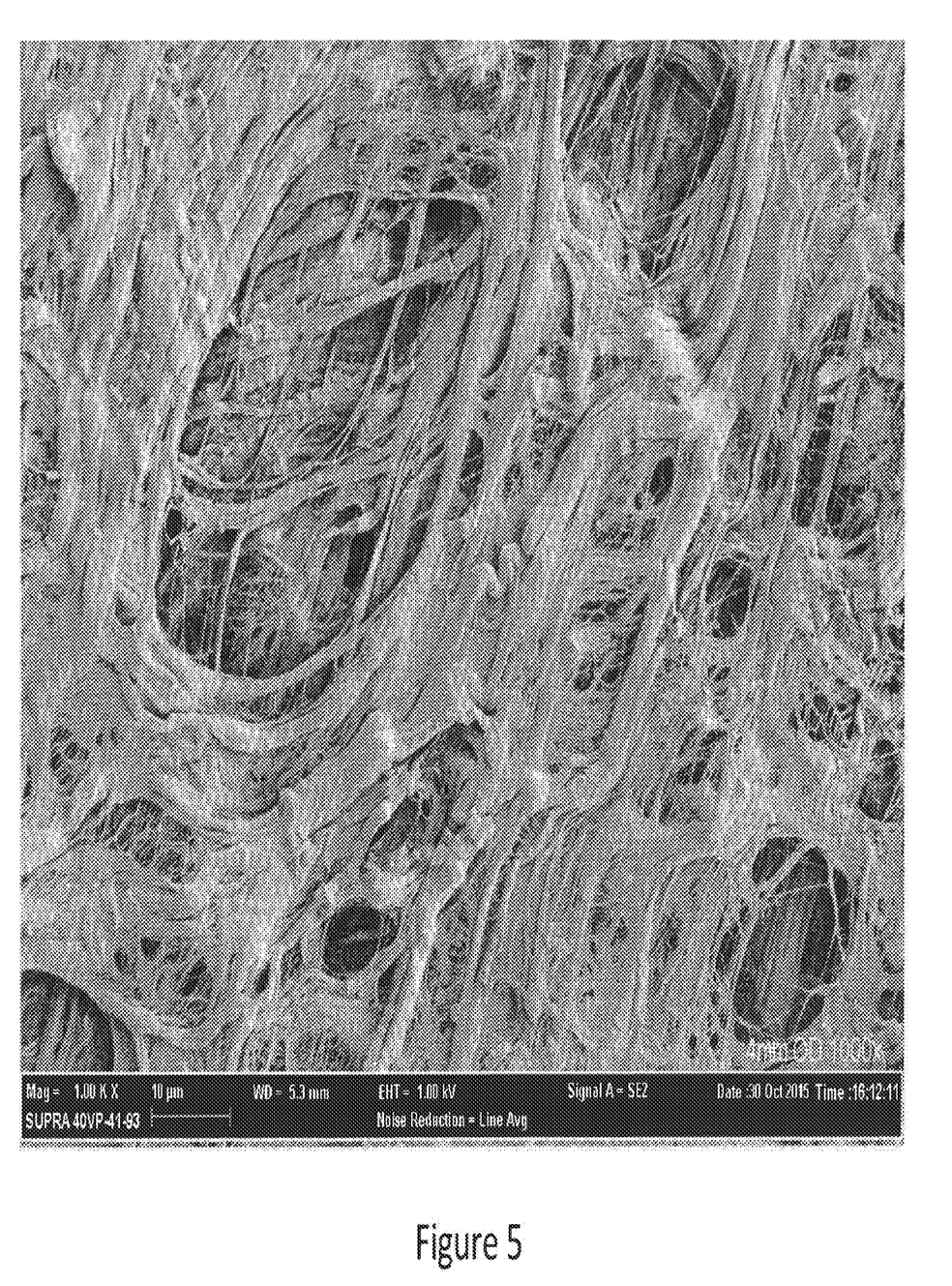
FIG. 5 is an SEM, at 1000× magnification, showing the porous structure of an exemplary embodiment of a drug delivery sleeve in a distended state.

As described, the first exemplary embodiment of sleeved balloon catheter 250 is arranged such that the drug is present only on the surface of balloon 202. During usage, drug delivery sleeve 100 acts to protect the drug on balloon 202 from being washed away by fluids encountered during the procedure and to protect the drug from being abraded from contact with any structure encountered during the procedure other than the targeted site of disease. Functionally, once navigated successfully to the intended site, balloon 202 may be inflated, causing drug delivery sleeve 100 to distend, opening its porous structure and allowing the drug to release and interact accordingly with the diseased tissue. FIG. 4 shows a scanning electron micrograph (SEM) of the porous structure of the described embodiment of drug delivery sleeve 100 in its native state, prior to any distention. FIG. 5 shows an SEM of the porous structure of the described embodiment of drug delivery sleeve 100 after distention to an inner diameter of 4 mm. The SEM's of FIGS. 4 and 5 are both taken at the same magnification (1000×). Comparing the structures of FIGS. 4 and 5, it is evident that the structure of FIG. 5 (after 4 mm distention) is more open than that of FIG. 4 (prior to any distention).

In certain instances it may be beneficial to treat sleeve 100, by any suitable means, in a manner which would facilitate the passing of fluids through the sleeve in its native state so as to provide a more effective drug release during distention. For example, if the drug utilized is in a solid or semi-solid form and would benefit from some time in contact with fluid in order to pass more easily through the porous sleeve structure. If, on the other hand, the drug utilized is already of a form that can readily pass through the sleeve structure, a treatment which would provide additional sealing to drug delivery sleeve 100 prior to distention may be desired. Such treatments may include, for example, the application of various coatings and/or any suitable means of altering the surface characteristics of sleeve 100.

Although certain embodiments of drug delivery sleeve 100 utilize balloon catheter 200 as a means of navigating and actuating the sleeve, any suitable device capable of navigating the sleeve to a specific site and capable of actuating the sleeve so as to suitably release the drug may be employed. For example, certain catheter based mechanical systems capable of distending sleeve 100 may be used. In certain situations, drug delivery sleeve 100 may, for example, be combined with a memory shape metallic scaffold capable distending the sleeve.

In a second embodiment of drug delivery balloon catheter 250, drug may be placed onto the surface of balloon 202 as well as onto the inner surface and into the porous structure of drug delivery sleeve 100. Drug delivery sleeve 100 may incorporate any drug suited to the treatment of any particular disease(s). For instance, drug delivery sleeve 100 may incorporate drugs and/or therapeutic agents or combinations of drugs and/or therapeutic agents such as but not limited to heparin, anti-platelet agents, platelet derived growth agents, antibiotics, steroids, agents that inhibit cell growth of all types, agents that inhibit cell division, agents that enhance cell growth of all types, and seed and/or progenitor cells of all types. Additionally, drug delivery sleeve 100 may include drugs and/or therapeutic agents of any suitable form. For example, drug delivery sleeve 100 may incorporate drugs and/or therapeutic agents or combinations of drugs and/or therapeutic agents having gelatinous forms of varying hardness and flexibility, or in some cases may incorporate a powdered form, or forms comprising a polymeric coating.

A length of drug delivery sleeve 100 may be fitted coaxially within an open-structured constraining tube having an inner diameter equal to or slightly larger than the outer diameter of sleeve 100. One end of drug delivery sleeve 100 is sealed closed by any suitable means, for example by tying, or heat sealing, or by ligating with thread. A blunt needle fitted with a luer adapter, having an outer diameter equal to or slightly larger than the inner diameter of drug delivery sleeve 100 is inserted into the other end of sleeve 100. A seal is formed between the needle and the sleeve by any suitable means, for example by wrapping with PTFE tape and ligating with thread, or by sealing with adhesive. The needle is connected to a syringe filled with, for example, a drug solution which is injected into drug delivery sleeve 100 with sufficient pressure to infiltrate the porous structure. The open-structured constraining tube keeps drug delivery sleeve 100 from distending while allowing the drug solution to at least partially penetrate the porous structure, and more preferably, to completely pass through and saturate the porous structure to the extent that droplets of the solution form on the outer surface of sleeve 100. Once the inner surface and structure of drug delivery sleeve 100 are satisfactorily treated with drug solution, the sleeve may be removed, placed on a small diameter rod of suitable dimensions and allowed to dry under any suitable conditions.

Many processes for the coating or treating of material surfaces with drugs are well known and commonly practiced. Such processes necessarily account for several variables such as but not limited to solution viscosity, physical and chemical characteristics of the drug, type of solvent utilized, introduction of polymerizing compounds, physical characteristics of the material being coated and surface chemistry of the material being coated. The details associated with such variables, all at play simultaneously, are beyond the scope of the present invention, drug delivery sleeve 100. Thus, the above exemplary process of coating drug delivery sleeve 100 with a drug is presented in a cursory manner, leaving the exactness of detail to those of skill in that art. One company that has extensive expertise in the art of drug coatings is SurModics, Inc., located in Eden Prairie, Minn. Other exemplary coating/treating processes included herein may also be presented in a cursory manner.

Following essentially the same procedure as that described in the previous embodiment of drug delivery balloon catheter 250, the drug coated drug delivery sleeve 100 of the present embodiment is attached to balloon catheter 200 as follows. A length of drug delivery sleeve 100 is cut such that the sleeve is longer than the length of balloon 202 plus the lengths of distal and proximal balloon seals 204 and 206 respectively. The length of drug delivery sleeve 100 is fitted coaxially over balloon 202 and balloon seals 204 and 206. Once properly situated, drug delivery sleeve 100 is attached to inner catheter member 208 to form distal sleeve attachment 102 and attached to outer catheter member 210 to form proximal sleeve attachment 104. With drug delivery sleeve 100 attached to balloon catheter 200, a second exemplary embodiment of a drug delivery balloon catheter 250 is completed wherein balloon 202 and drug delivery sleeve 100 are both coated with a drug.

As described, this second exemplary embodiment of sleeved balloon catheter 250 is arranged such that both the surface of balloon 202 and the inner surface as well as the porous structure of drug delivery sleeve 100 are coated with a drug. Similar to the previous first embodiment, during usage, drug delivery sleeve 100 of this second embodiment acts to protect the drug on balloon 202 from being washed away by fluids encountered during the procedure and to protect the drug from being abraded from contact with any structure encountered during the procedure other than the targeted site of disease. This second exemplary embodiment provides additional drug stored within the structure of the drug delivery sleeve 100 as well as on its inner surface. Functionally, once navigated successfully to the intended site, balloon 202 may be inflated, causing drug delivery sleeve 100 to distend, opening its porous structure and allowing the drug to release and interact accordingly with the diseased tissue. The additional drug on and within drug delivery sleeve 100 is advantageous not only because of the increase in quantity, but also because the drug within the sleeve structure, while being protected as described, is closer to the outer surface of the sleeve (compared to the first exemplary embodiment of sleeved balloon catheter 250) and thus has a more direct path to contact the site of disease.

If it is deemed by any suitable measure that the drug and/or therapeutic agent associated with the various surfaces of sleeve 100 is sufficient to effectively treat the disease site, the drug on the surface of balloon 202 may be omitted.

It should be noted that the process described above for coating the inner surface and structure of drug delivery sleeve 100 with drug may be reversed so that the outer surface and structure of the sleeve are coated. This may be achieved by replacing the open-structure constraining tube placed on the outside of drug delivery sleeve 100 with an open-structure support tube situated on the inside of the sleeve. With the sleeve 100 supported on the inside, the assembly of the sleeve with one end sealed and the other attached to a needle may be placed in a bath of drug solution. The needle may be attached to a syringe or any suitable means of applying negative pressure; the negative pressure causing the drug solution to pass from the outside of drug delivery sleeve 100, through the porous structure and into the inner volume of the sleeve, eventually filling the sleeve entirely.

In alternative embodiments of drug delivery balloon catheter 250, drug delivery sleeve 100 may comprise porous circumferentially distensible tubes as described by U.S. Pat. No. 5,800,522 to Campbell, et al, which is included herein by reference. Such alternative embodiments may be produced by generally following the steps outlined in the description of the previous two embodiments of drug delivery balloon catheter 250 but replacing the circumferentially distensible polyethylene tubes comprising the preferred embodiment of drug delivery sleeve 100 with the tubes taught by U.S. Pat. No. 5,800,522. In such alternative embodiments, since the circumferentially distensible tubes taught by U.S. Pat. No. 5,800,522 are produced from expanded PTFE (ePTFE), certain of the previously described attachment techniques, such as thermal bonding, may be less viable.

Heretofore each of the described embodiments of drug delivery sleeve 100 has been in the form of a circumferentially distensible porous tube which exhibits negligible degrees of recoil after distention. Thus, each of the embodiments of drug delivery sleeve 100 described so far, after being distended by underlying balloon 202 remain substantially in their distended form. In certain situations, for certain applications, it may be desirable to utilize a drug delivery sleeve 100 which has a high degree of recoil. In such instances, an elastomeric material may be used to create an embodiment of drug delivery sleeve 100.

A second exemplary embodiment of drug delivery sleeve 100 may comprise, for example, a thin walled silicone tube. For this elastic embodiment of drug delivery sleeve 100, it may be advantageous to use an embodiment of balloon catheter 200, with balloon 202, produced from the same or similar material. For example, balloon catheter 200 may comprise an embolectomy balloon catheter wherein balloon 202 as well as the catheter member(s) are each made of silicone. The embolectomy balloon 202 may, for example, be capable of being inflated to a diameter of 4 mm. The silicone tube comprising drug delivery sleeve 100 may have an inner diameter equal to or slightly larger than the outer diameter of balloon 202 and a wall thickness of about 0.1 to 0.05 mm and in certain instances, more preferably, 0.05 to 0.03 mm. The silicone tube preferably exhibits similar elongation/elastic characteristics as balloon 202 and may be produced by any suitable means such as but not limited to extrusion or dip molding. One manufacturer of such embolectomy balloon catheters and silicone tubing is Specialty Silicone Fabricators, headquartered in Tustin, Calif. A length of the silicone tube may be coaxially fitted onto a stainless steel rod having an outer diameter equal to or slightly smaller than the inner diameter of the silicone tube. Once on the rod, the silicone tube may have a pattern laser cut through its wall. The laser cut pattern renders the silicone tube comprising this second embodiment of drug delivery sleeve 100 porous.

Figure 6:
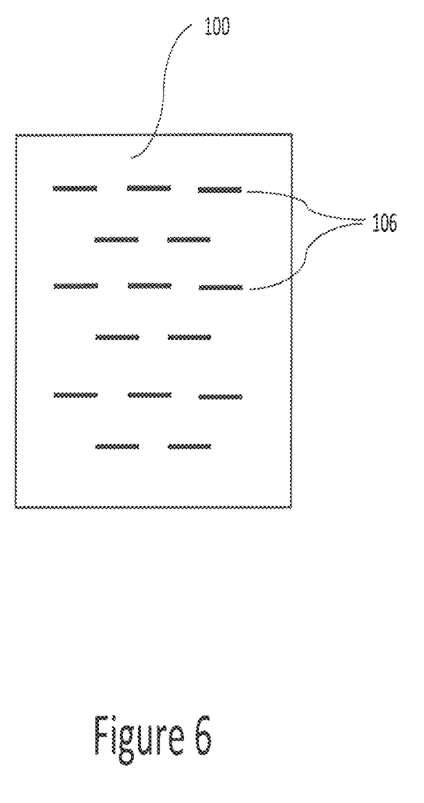
FIG. 6 is a close up view of an exemplary embodiment of a drug delivery sleeve with laser cut pattern in its native state, prior to distention.

FIG. 6 shows a close up illustration of an exemplary laser pattern cut through the wall of this embodiment of drug delivery sleeve 100 with the drug delivery sleeve in its native state, prior to any distention. The openings cut through the wall of drug delivery sleeve may have any suitable geometry, for example, circles, hexagons, lines and or squares. Further, the laser pattern may suitably employ combinations of opening geometries. As shown in FIG. 6, an exemplary laser pattern comprises a matrix of slots 106 arranged in an offset pattern. Slot(s) 106 may have any suitable dimensions, such as, for example, a nominal length of 45µ (measured along the major axis of drug delivery sleeve 100) and a nominal width of 15µ (measured along a transverse axis of drug delivery sleeve 100) depending upon, for example, characteristics of the drug to be delivered. The matrix pattern of slots 106 may likewise have any suitable dimensions, such as, for example, a spacing of about 0.2 mm between consecutive slots 106 (measured along the major axis of drug delivery sleeve 100) and a rotational spacing of about 36° (measured with drug delivery sleeve 100 rotating about its major axis) between consecutive slots 106 radially. The exemplary matrix pattern may be laser cut by any suitable process. One such process may be performed by Lenox Laser, located in Glen Arm, Md.

With the pattern of slots 106 cut into the embodiment of drug delivery sleeve 100, the sleeve may be attached to balloon catheter 200. In this embodiment of balloon catheter 200, the catheter member, made from silicone, may comprise a single tube having a fixed wire configuration. In a fixed wire configuration, the catheter member includes a single lumen for inflation of balloon 202 and a metallic wire resident within the wall of the catheter member for support.

The exemplary embodiment of drug delivery sleeve 100 may be arranged over balloon 202 as described in the previous embodiments of drug delivery balloon catheter 250 and may be attached by any suitable means. In this particular embodiment, since drug delivery sleeve 100 is made from silicone and balloon 202, as well as the fixed wire tubular catheter member, are also made from silicone, the use of a silicone based adhesive may be preferred.

As described, this third exemplary embodiment of sleeved balloon catheter 250 is arranged such that the drug is present on the surface of balloon 202. During usage, drug delivery sleeve 100 acts to protect the drug on balloon 202 from being washed away by fluids encountered during the procedure and to protect the drug from being abraded from contact with any structure encountered during the procedure other than the intended site of disease. Functionally, once navigated successfully to the targeted site, balloon 202 may be inflated, causing drug delivery sleeve 100 to distend, opening slots 106 and allowing the drug to release and interact accordingly with the diseased tissue. In this third embodiment of sleeved balloon catheter 250, since the balloon 202 and drug delivery sleeve 100 are both made from silicone, a highly elastic material, upon deflation both balloon 202 and drug delivery sleeve 100 return substantially to their preinflated/predistended dimensions, exhibiting a high degree of recoil.

Figure 7:
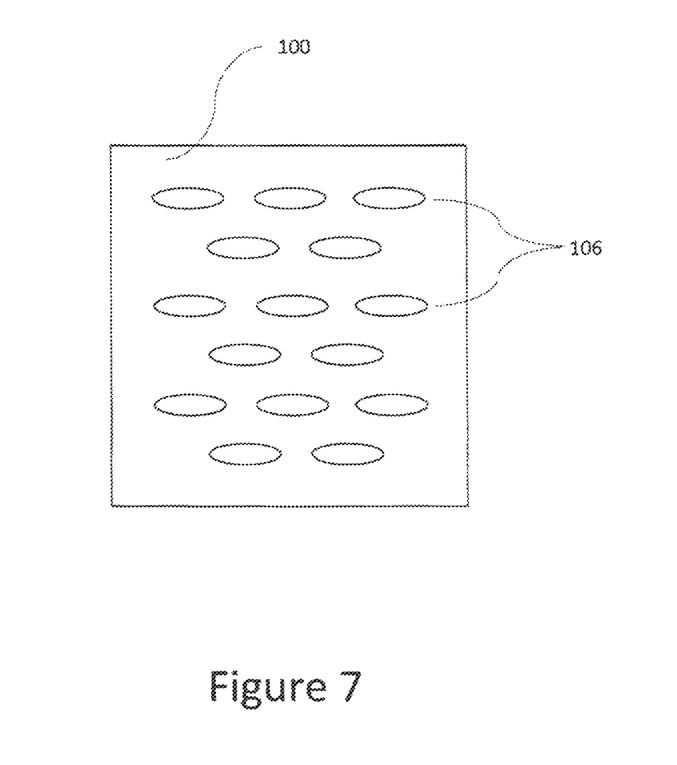
FIG. 7 is a close up view of an exemplary embodiment of a drug delivery sleeve with laser cut pattern in a distended state.

FIG. 7 shows a close up illustration of the same exemplary laser pattern as FIG. 6, but with drug delivery sleeve 100 in a distended state. Comparing the geometry of slots 106 between FIGS. 6 and 7, it is evident that in the distended state, (shown in FIG. 7) the slots 106 enlarge, assuming a generally elliptical form in accordance with the degree of circumferential growth.

The same second exemplary embodiment of drug delivery sleeve 100, comprising a laser cut silicone tube may also be combined with a balloon catheter 200 such as utilized in the first exemplary embodiment of drug delivery balloon catheter 250, wherein balloon 202 is drug coated. The general construction procedure and attachment may be as previously described, however, since silicone is a material that is not typically encountered in peripheral balloon angioplasty catheters, and is typically not melt processable, certain methods of attachment, such as thermal bonding, may be less viable.

In operation, this fourth exemplary embodiment of drug delivery balloon catheter 250 would function in a manner similar to the previously described exemplary embodiments. This fourth exemplary embodiment, wherein the blow molded balloon 202 is covered by a highly elastic, high recoil, silicone drug delivery sleeve 100 may offer the advantage of providing an improved, smaller, profile of balloon 202 (and thus the overall device) upon deflation.

It should be noted that although these third and fourth exemplary embodiments of drug delivery balloon catheter 250 have the drug applied to the underlying balloon 202, the exemplary silicone drug delivery sleeve 100 may be coated/treated as well. The coating may be accomplished in a fashion similar to the general process described in the second exemplary embodiment of drug delivery balloon catheter 250 above, however since the silicone material may be inherently less porous than a porous polyethylene film, it may be advantageous to distend silicone drug delivery sleeve 100 by some degree during the coating process. The distention, as shown in FIG. 7 would cause an opening of slot(s) 106, thereby allowing more drug solution to flow into the drug delivery sleeve 100. In certain instances, depending on the elasticity required, in order to maximize the porosity the exemplary silicone drug delivery sleeve 100, it may be desirable to make the sleeve from porous silicone. The use of other porous elastomeric materials, such as, for example, porous polyurethane may also be advantageous.

As described above, a balloon catheter may be used as a means of navigation and distention of drug delivery sleeve 100. However, in certain cases it may be advantageous to utilize an alternative means of navigation and distention. For example, if it is preferred to maintain the flow of blood or any other bodily fluid through the vessel or structure being treated. In such instances devices such as wire baskets typically used in ureteroscopy procedures may be suitably adapted to provide enough dilation force to distend sleeve 100 as described. The adaptation may require the use of a larger number of wires to form the basket or wires of a larger diameter. One such wire basket device is the LithoCatch Wire Basket manufactured by Boston Scientific, Inc., headquartered in Marlborough, Mass. Various endoscopic and/or laparoscopic devices may also be modified to provide an effective means of navigation and distention of drug delivery sleeve 100. The design and manufacture of laparoscopic, endoscopic and catheter based devices of this nature is well understood.

In certain situations, for example, if sleeve 100 is combined with a device which does not include a balloon component, an embodiment of drug delivery sleeve 100 that combines porous and substantially nonporous materials may be desirable. In the absence of a balloon, during distention, drug delivery sleeve 100 may not be fully supported on its interior surface. If the sections of the interior surface of sleeve 100 are unsupported, then during distention, at those unsupported sections, it would be possible for the drug or therapeutic agent to be released inwardly, or at least partially inwardly, away from the site of disease. In some cases, this may be acceptable, however, to maximize the outward release of the drug or therapeutic agent, a nonporous layer or a layer that does not allow the drug to pass through it, situated on the interior surface of sleeve 100 would be beneficial.

A third embodiment of drug delivery sleeve 100 may comprise a thin walled elastomeric tube, with a thin layer of foam or sponge-like material adhered to its outer surface. The thin walled elastomeric tube may be produced of any suitable material, by any suitable method, for example, silicone tubing, such as previously described. Similarly, the foam layer may be produced of any suitable material. In this exemplary embodiment, polyurethane foam, which is commercially available from several sources may be used. One supplier of such foam tubing is Essentra Porous Technologies, located in Colonial Heights, Va.

A length of thin polyurethane foam tubing of inner diameter equal to or slightly larger than the outer diameter of the silicone tubing may be coaxially fitted over the silicone tube. The foam may be bonded to the silicone tube by any suitable means. In this embodiment, the use of a silicone based adhesive may be preferred. With the silicone tubing and the foam tubing bonded, drug may be applied onto the surface and into the structure of the foam by any suitable means. In some instances it may be more preferred to apply the drug/therapeutic agent to the polyurethane foam tube prior to bonding it with the silicone tube. Regardless of when the drug/therapeutic agent is applied, once completed, this third exemplary embodiment of drug delivery sleeve 100, making use of highly elastic/high recoil materials, is capable of a large range of distention. After distention, the exemplary embodiment of drug delivery sleeve 100 returns substantially to its native/predistended dimensions.

In a manner similar to the previously described embodiments, this exemplary third embodiment of drug delivery sleeve 100 acts as a means of minimizing drug losses, as a reservoir for drugs and/or therapeutic agents and provides a means of controlled release. Once navigated to the targeted disease site, the silicone tubing of sleeve 100, during distention, applies pressure to the foam tubing, causing the foam tubing to distend and also to compress between the silicone tubing and the surface of the disease site. The distention, coupled with the compression of the foam tubing results in a controlled drug release, the drug contacting the disease site directly and under some degree of pressure.

A drug delivery sleeve according to various aspects of the present disclosure may be suitable for the treatment of disease within coronary and peripheral blood vessels, as well as within the neurovasculature, and various other bodily conduits and structures. Utilized in cooperation with balloon catheters and/or other devices, the described drug delivery sleeves act as a means of reducing drug losses as well as acting as a reservoir for holding the drug and providing a controlled mechanism for the release of the drug.

It is to be understood that changes and modifications may be made to the various exemplary embodiments described herein. Changes and modifications may include, for example, changes in the type and/or design of balloon catheters, changes to the diameters and lengths of balloon catheters and drug delivery sleeves, changes to materials or combinations of materials used to manufacture the balloon catheters and drug delivery sleeves, changes in materials and/or methods utilized in the attachment of drug delivery sleeves to balloon catheters, variations of drug type and/or the physical form of the drug and variations of the methods used in coating/treating balloon catheters and drug delivery sleeves with the drug. Additionally, the drug delivery sleeve may, in certain instances, be used cooperatively with devices other than balloon catheters. Any suitable device capable of navigating the sleeve to a specific site and capable of actuating the sleeve so as to suitably release the drug may be employed. Thus, any such changes and/or modifications are intended to be included within the scope of the present invention as set forth in the appended claims.

What is claimed is:

1. A method for making a system for delivering a first therapeutic agent within a bodily conduit, comprising:
   associating the first therapeutic agent with an inflatable balloon; and
   positioning a sleeve over the inflatable balloon at a location that at least covers the first therapeutic agent as associated with the inflatable balloon, wherein the sleeve that is positioned over the inflatable balloon at the location that at least covers the first therapeutic agent includes at least one layer of porous material, comprised of a plurality of microstructural elements and having a native porosity, wherein the plurality of microstructural elements of at least a portion of the at least one layer of porous material are arranged to decrease the native porosity of the at least one layer of porous material to inhibit the first therapeutic agent from being released through the at least one layer of porous material when the inflatable balloon and the sleeve are inserted within the bodily conduit and to allow the first therapeutic agent to be released through the at least one layer of porous material for delivery at the desired location within the bodily conduit, via spacings that are formed between adjacent ones of the arranged plurality of microstructural elements, when the sleeve is subsequently caused to be distended by use of an expansion device cooperable with the inflatable balloon.

2. The method as recited in claim 1, further comprising thermally and physically manipulating the at least one layer of porous material to decrease the native porosity of the at least one layer of porous material.

3. The method as recited in claim 1, further comprising bonding together a plurality of layers of porous film material to form the at least one layer of porous material.

4. The method as recited in claim 1, further comprising attaching at least an end of the sleeve to a part of the expansion device.

5. The method as recited in claim 1, wherein associating the first therapeutic agent with the inflatable balloon comprises placing the first therapeutic agent on at least a portion of an outer surface of the inflatable balloon.

6. The method as recited in claim 1, wherein the first therapeutic agent is selected from a group consisting of heparin, anti-platelet agents, platelet derived growth agents, antibiotics, steroids, agents that inhibit cell growth of all types, agents that inhibit cell division, agents that enhance cell growth of all types, and seed and/or progenitor cells.

7. The method as recited in claim 1, further comprising associating the first therapeutic agent with the sleeve in addition to associating the first therapeutic agent with the inflatable balloon.

8. The method as recited in claim 7, wherein associating the first therapeutic agent with the sleeve comprises placing the first therapeutic agent on at least a portion of an outer surface of the sleeve.

9. The method as recited in claim 7, wherein associating the first therapeutic agent with the sleeve comprises infiltrating the first therapeutic agent within pores of the sleeve.

10. The method as recited in claim 7, wherein the first therapeutic agent is selected from a group consisting of heparin, anti-platelet agents, platelet derived growth agents, antibiotics, steroids, agents that inhibit cell growth of all types, agents that inhibit cell division, agents that enhance cell growth of all types, and seed and/or progenitor cells.

11. The method as recited in claim 1, further comprising associating a second therapeutic agent different than the first therapeutic agent with the sleeve.

12. The method as recited in claim 11, wherein associating the second therapeutic agent with the sleeve comprises placing the second therapeutic agent on at least a portion of an outer surface of the sleeve.

13. The method as recited in claim 11, wherein associating the second therapeutic agent with the sleeve comprises infiltrating the second therapeutic agent within pores of the sleeve.

14. The method as recited in claim 11, wherein the first therapeutic agent and the second therapeutic agent are each selected from a group consisting of heparin, anti-platelet agents, platelet derived growth agents, antibiotics, steroids, agents that inhibit cell growth of all types, agents that inhibit cell division, agents that enhance cell growth of all types, and seed and/or progenitor cells.

15. The method as recited in claim 1, further comprising providing a treatment to the sleeve to inhibit a passing of a bodily fluid through the sleeve in a non-distended state of the sleeve.

16. The method as recited in claim 1, further comprising decreasing the native porosity of the at least one layer of porous material by causing the plurality of microstructural elements of at least a portion of the at least one layer of porous material to be generally linearly aligned to thereby reduce a spacing therebetween to a degree that will inhibit the first therapeutic agent from being released through the at least one layer of porous material when the inflatable balloon and the sleeve are inserted within the bodily conduit.

17. The method as recited in claim 16, wherein associating the first therapeutic agent with the inflatable balloon comprising placing the first therapeutic agent on at least a portion of an outer surface of the inflatable balloon.

18. The method as recited in claim 17, wherein the first therapeutic agent is selected from a group consisting of heparin, anti-platelet agents, platelet derived growth agents, antibiotics, steroids, agents that inhibit cell growth of all types, agents that inhibit cell division, agents that enhance cell growth of all types, and seed and/or progenitor cells.

19. The method as recited in claim 16, further comprising associating the first therapeutic agent with the sleeve in addition to associating the first therapeutic agent with the inflatable balloon.

20. The method as recited in claim 19, wherein associating the first therapeutic agent with the sleeve comprising placing the first therapeutic agent on at least a portion of an outer surface of the sleeve.

21. The method as recited in claim 19, wherein associating the first therapeutic agent with the sleeve comprising infiltrating the first therapeutic agent within pores of the sleeve.

22. The method as recited in claim 19, wherein the first therapeutic agent is selected from a group consisting of heparin, anti-platelet agents, platelet derived growth agents, antibiotics, steroids, agents that inhibit cell growth of all types, agents that inhibit cell division, agents that enhance cell growth of all types, and seed and/or progenitor cells.

23. The method as recited in claim 16, further comprising associating a second therapeutic agent different than the first therapeutic agent with the sleeve.

24. The method as recited in claim 23, wherein associating the second therapeutic agent with the sleeve comprises placing the second therapeutic agent on at least a portion of an outer surface of the sleeve.

25. The method as recited in claim 23, wherein associating the second therapeutic agent with the sleeve comprises infiltrating the second therapeutic agent within pores of the sleeve.

26. The method as recited in claim 23, wherein the first therapeutic agent and the second therapeutic agent are each selected from a group consisting of heparin, anti-platelet agents, platelet derived growth agents, antibiotics, steroids, agents that inhibit cell growth of all types, agents that inhibit cell division, agents that enhance cell growth of all types, and seed and/or progenitor cells.

27. The method as recited in claim 16, further comprising providing a treatment to the sleeve to facilitate a passing of a bodily fluid through the sleeve in a non-distended state of the sleeve.

28. The method as recited in claim 16, further comprising providing a treatment to the sleeve to inhibit a passing of a bodily fluid through the sleeve in a non-distended state of the sleeve.

29. The method as recited in claim 1, further comprising providing the sleeve with a plurality of laser cut openings.

\* \* \* \* \*